(12) United States Patent
Chen

(10) Patent No.: US 9,737,282 B2
(45) Date of Patent: Aug. 22, 2017

(54) METHOD, DEVICE AND SYSTEM FOR DETERMINING THE OPEN/CLOSED SWITCH MOMENT OF AN ARTERY OF INTEREST UNDER A CHANGING PRESSURE

(75) Inventor: Yinan Chen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 735 days.

(21) Appl. No.: 14/130,329

(22) PCT Filed: Jul. 5, 2012

(86) PCT No.: PCT/IB2012/053435
§ 371 (c)(1),
(2), (4) Date: Feb. 14, 2014

(87) PCT Pub. No.: WO2013/005179
PCT Pub. Date: Jan. 10, 2013

(65) Prior Publication Data
US 2014/0148702 A1    May 29, 2014

(30) Foreign Application Priority Data

Jul. 5, 2011 (WO) ................ PCT/CN2011/076846

(51) Int. Cl.
*A61B 8/00* (2006.01)
*A61B 8/08* (2006.01)
(Continued)

(52) U.S. Cl.
CPC ............ *A61B 8/0891* (2013.01); *A61B 5/022* (2013.01); *A61B 5/02007* (2013.01); *A61B 8/06* (2013.01); *A61B 8/5223* (2013.01); *A61B 8/488* (2013.01)

(58) Field of Classification Search
None
See application file for complete search history.

(56) References Cited

U.S. PATENT DOCUMENTS

| 4,425,922 A | 1/1984 | Conti et al. |
| 6,520,919 B1 | 2/2003 | Nunome et al. |
| 2008/0269621 A1 | 10/2008 | Mao |

FOREIGN PATENT DOCUMENTS

EP      1400201 A1    3/2004

*Primary Examiner* — Jonathan Cwern

(57) ABSTRACT

The method of determining the open/closed switch moment of an artery of interest under a changing pressure comprises: detecting a first Doppler ultrasound signal from the blood flow in the artery of interest using a first Doppler ultrasound transducer, which is placed on the artery of interest in one limb which is provided with a cuff that is capable of being inflated or deflated to provide the changing pressure to the artery of interest; detecting a second Doppler ultrasound signal from the blood flow in a reference artery using a second Doppler ultrasound transducer, the reference artery being in any one of the other three limbs; deriving a third signal from the first Doppler ultrasound signal and the second Doppler ultrasound signal, the third signal indicating the degree of synchronism between the first Doppler ultrasound signal and the second Doppler ultrasound signal; and out-putting a fourth signal to indicate the artery of interest is closed or reopened at the moment when the third signal satisfies a predefined condition. By utilizing the second ultrasound signal as a reference and deriving a signal indicating the synchronization property between the two ultrasound signals, the open/closed status of the artery of interest under a changing pressure can be determined more stably and more reliably regardless of the detailed condition of the patient.

18 Claims, 6 Drawing Sheets

(51) Int. Cl.
*A61B 5/02* (2006.01)
*A61B 8/06* (2006.01)
*A61B 5/022* (2006.01)

METHOD, DEVICE AND SYSTEM FOR DETERMINING THE OPEN/CLOSED SWITCH MOMENT OF AN ARTERY OF INTEREST UNDER A CHANGING PRESSURE

CROSS REFERENCE TO RELATED APPLICATIONS

This application is the U.S. National Phase application under 35 U.S.C. §371 of International Patent Application No. PCT/IB2012/053435, filed Jul. 5, 2012, published as WO 2013/005179 on Jan. 10, 2013, which claims the benefit of International Patent Application Number PCT/CN2011/076846 filed Jul. 5, 2011. These applications are hereby incorporated by reference herein.

FIELD OF THE INVENTION

The invention relates to Doppler ultrasound, and particularly to a method, device and system for determining the open/closed switch moment of an artery of interest under a changing pressure.

BACKGROUND OF THE INVENTION

Doppler ultrasound is widely used to measure blood flow velocity in clinical applications. In a standard Doppler ultrasound blood flow measurement, an experienced doctor first selects an appropriately sized cuff and places it around the limb at a location above the artery of interest. The doctor needs to wait for the Doppler sound to become stable and rhythmic after the Doppler probe has been well placed over the artery. After that, the doctor inflates the cuff to gradually increase the cuff pressure till the Doppler sound disappears, which implies that the artery is already fully occluded. Important information is provided by the moment at which the status of the artery changes from open to closed (or vice versa) because this moment is very crucial for determining some parameters in the blood flow measurement. For example, the corresponding pressure read from the sphygmomanometer at the moment immediately before this switch moment (at which the status of the artery changes from open to closed) is defined as the inflation systolic blood pressure (SBP). The inflation SBP may be correctly measured if the open to closed switch moment is correctly determined.

Then, the doctor further inflates the cuff until the cuff pressure is 20 mmHg to 30 mm Hg over the inflation SBP, after which he slowly deflates the cuff until the Doppler sound reappears. Similarly, the corresponding pressure read from the sphygmomanometer at the moment when the doctor hears the first Doppler sound in the deflation process is defined as the deflation SBP, physiologically describing that the status of the artery changes from closed to reopened. Doppler ultrasound is used as the gold standard to determine the open/closed switch moment of an artery of interest and furthermore to measure the systolic pressure.

However, the automatic determining of the open/closed switch moment of an artery of interest under a changing pressure is only based on the change of a continuous ultrasonic signal. How to correctly detect the last sound in the inflation phase and the first sound in the deflation phase is a fundamental problem.

Conventionally, it could be mathematically summarized as a feature mapping problem. Inspired from the standard blood flow measurement, three typical parameters of blood flow, i.e. sufficient power of the sound, reasonable velocity of the blood flow and stable rhythm corresponding to the heart beat, are the straightforward features to map the open status of the artery. As long as one of the features has a sudden change during cuff inflation, i.e. outside of the feature threshold, the artery is deemed to be closed. For the cuff deflation phase, it is necessary to request a safe condition of first sound recognition, i.e. that all the features of the Doppler sound should be restored when the status of the artery changes from closed to reopened.

However, these three features mentioned above are not easily employed by a variety of the users, especially with respect to finding the proper thresholds to discriminate the two statuses of the artery for the patient with artery disease. All these features may change from person to person, even for the same person at different times, which causes the problem of false determination of the open/closed switch moment.

For example, the problem of using the power feature is that: because the distal stenosis for the patient with atherosclerosis is ischemic, the Doppler sound presents a low power property when the transducer is placed at the distal stenosis. However, for the same patient the power situation at the proximal stenosis differs from that at the distal stenosis. The power of sound is as high as that of the normal artery due to the power contribution from the turbulence and laminar flow around the site of stenosis. The amplitude of the sound power depends on the grade of artery stenosis, so that those skilled in the art cannot set one power threshold for all measurement cases. Furthermore, low power creates an unapparent power boundary between the open and closed status of the artery, making it difficulty to set a valid power threshold. The situation with respect to the patient with artery calcification is similar to the low power situation. It is usually hard to find a steady duration in which the power is obviously low, because the artery of a patient with artery calcification cannot be fully occluded.

Further, the problem of using the velocity of the blood flow may be as follows: a few factors may affect the measured velocity of the blood flow. With regard to hemodynamics, these factors include: diameter of the artery, consistency of the blood and stiffness of the artery wall. The hemodynamic parameters will be deformed by the state of illness of the patient. With respect to operational work, the main factor that influences the observed value of the velocity of the blood flow is the transmission angle of the ultrasound. Because of the variability of the blood flow velocity, the velocity threshold to discriminate the status of the artery should be customized for different users, which makes the algorithm very complicated.

Furthermore, the problem of using the sound periodicity is that: the subject's heart rate is highly related to the periodicity of the Doppler signal. A person's heart beat is sensitive to his emotions and stimuli from external circumstances. It is really common that a person's heart rate accelerates from 80 bpm to 120 bpm when he feels nervous or uncomfortable. This may also happen during the blood flow measurement. Although the subject's heart beat can be estimated in the calibration stage, the heart rate of normal persons will likely vary a lot as the cuff pressure increases or decreases, quite unlike a patient with arrhythmia. The degree of rhythmic alteration is unpredictable beforehand, so that it is really hard to set the periodicity threshold well in the case of people who easily feel nervous or distressed. If the rhythmic alteration is underestimated or overestimated, the estimated switch moment will correspondingly have a positive or negative lag.

It can be seen from the above that an important reason why the above-mentioned problems cannot easily be solved is that it is impossible to describe the behavior of the subject's blood flow without any calibration procedure as well as to adapt the algorithm for the change during the measurement using the calibration forecast.

The conventional method is not usable to determine the precise switch moment for the patient with artery calcification, stenosis and arrhythmia. If a method focuses on the change of the power of the Doppler sound, the method has an error risk because the power change may be extremely small in the case of the patient with the artery calcification or stenosis. If a method focuses on the change of the period of the Doppler sound, the method cannot be effective in the cases where the subject is a patient with arrhythmia or a person whose heart rate is easily disturbed.

In view of the above, there is a need for a method which adopts more effective and adaptive features so as to make the determination of the switch moment more reliable, and which method is adaptable to a wide range of uses, including even patients with artery diseases, such as arrhythmia, artery stenosis and calcification.

SUMMARY OF THE INVENTION

This invention makes it possible to overcome the limitations of previous algorithms in certain user bases.

The inventor realizes that the blood flows in any two arteries are highly correlated and synchronized with each other because they actually come from the same pulsation of a human's heart. This phenomenon also applies to persons with artery calcification, stenosis or arrhythmia. Based on this realization, the inventor deduces a feature which can describe the artery status of the subjects in this invention in a more stable and more general manner. This method can further be utilized to realize the automation, accuracy and generalization of SBP measurement.

Specifically, dual Doppler ultrasounds are used to sense the blood flow for the automatic ABI (ankle—brachial index) measurement. A cuff is worn on one of the limbs for unilateral ABI measurement. The first Doppler ultrasound transducer should be placed on the artery of interest on the side of the limb wearing the cuff that is capable of being inflated or deflated to provide the changing pressure to the artery of interest. The second Doppler ultrasound transducer should be placed on the reference artery where blood freely flows during the whole measurement. In other words, the second Doppler ultrasound transducer should be placed on another artery in any one of the other three limbs without the effect from the cuff being inflated or deflated.

Processing of the dual Doppler ultrasounds should be enabled at the same time, so that the waveforms from the blood flows in the two arteries detected by using the dual Doppler ultrasounds should be in synchronism with each other. This synchronism is lost when the cuff finally occludes the artery of interest, and this indicates that the status of the artery of interest changes from open to closed. In this manner, the method proposed by the present invention would improve the feasibility and accuracy of determining the artery status switch moment in various clinical environments/conditions.

The present invention provides a method and a device for determining the open/closed switch moment of an artery of interest under a changing pressure to fulfill the above concept.

According to one aspect of the present invention, it provides a method of determining the open/closed switch moment of an artery of interest under a changing pressure, comprising the steps of:

detecting a first Doppler ultrasound signal from the blood flow in the artery of interest using a first Doppler ultrasound transducer, which is placed on the artery of interest in one limb wearing a cuff that is capable of being inflated or deflated to provide the changing pressure to the artery of interest;

detecting a second Doppler ultrasound signal from the blood flow in a reference artery using a second Doppler ultrasound transducer, the reference artery being in any one of the other three limbs;

deriving a third signal from the first Doppler ultrasound signal and the second Doppler ultrasound signal, the third signal indicating the degree of synchronism between the first Doppler ultrasound signal and the second Doppler ultrasound signal; and outputting a fourth signal to indicate the artery of interest is closed or reopened at the moment when the third signal satisfies a predefined condition.

In the method of the present invention, since the blood flows in two arbitrary arteries are highly correlated and synchronized with each other because they are actually coming from the same pulsation of a person's heart, if the first Doppler ultrasound transducer is placed on the artery of interest on the side of the limb wearing the cuff, the second ultrasound transducer, which is placed on the reference artery where blood freely flows during the whole measurement, can be used to detect a reference Doppler ultrasound signal in addition to the first Doppler ultrasound signal detected by the first Doppler ultrasound transducer.

By deriving the third signal indicating the synchronization property between the two Doppler ultrasound signals detected by the two transducers, it is possible to determine the status switch moment of the artery of interest in a more stable and more reliable manner regardless of the detailed condition of the subjected users. Furthermore, if this method is utilized in SBP measurement, the SBP can be measured in a more stable and more reliable manner regardless of the detailed condition of the subjected users, for the same reason.

In an embodiment of the present invention, the third signal is derived from the cross-covariance property between the first ultrasound signal and the second ultrasound signal.

In this embodiment, the method of the present invention adopts the cross-covariance property, which is a good indicator of the degree of synchronism. The signal from the first ultrasound transducer correlates well with the signal from the second ultrasound transducer till the measured artery is fully occluded by the cuff pressure. Accordingly, losing and recovering the high correlation property between two signals represents the moments at which the status of the artery of interest switches from open to closed and from closed to reopened, respectively, due to the pressure change of the cuff.

Therefore, in accordance with this embodiment, a simple cross-covariance calculation is directly performed on the Doppler audio signal, and it can be easily calculated in the sound domain, rather than the frequency domain. The calculation time is speeded up so as to meet the real time requirement.

Of course, properties or approaches to determine the degree of synchronism other than the cross-covariance property may be used to implement the basic idea of the present invention. However, as mentioned above, compared with the cross-covariance property approach, other approaches to determine the degree of synchronism may involve complicated calculations in the frequency domain.

In a further embodiment of the present invention, the third signal comprises at least one of a cross-covariance coefficient of the first and the second ultrasound signals and a lag value of the first and the second ultrasound signals.

In this embodiment, the third signal satisfies the predefined condition if the cross-covariance coefficient is less than 20% of the mean value of the previous values or abs(Lc−Lp)>w*Lp, wherein Lc is the lag in the current time window, Lp is the mean of the lags acquired previously, and w is the adjustable coefficient of the asynchronous tolerance, and therefore it indicates that the two ultrasound signals lose the high correlation property at the moment at which the status of the artery of interest switches from open to closed.

Accordingly, the step of outputting comprises outputting the fourth signal to indicate the artery of interest is closed at this moment.

In a further embodiment of the present invention, the third signal may comprise both a cross-covariance coefficient of the first and the second Doppler ultrasound signals and a lag value of the first and the second Doppler ultrasound signals, and the third signal satisfies the predefined condition if both the cross-covariance coefficient is higher than 20% of the mean value of the previous values and abs(Lc−Lp)<w*Lp, wherein Lc is the lag in the current time window, Lp is the mean of the lags acquired previously, and w is the adjustable coefficient of the asynchronous tolerance, and therefore it indicates that the two ultrasound signals recover to have a high correlation property at the moment at which the status of the artery of interest switches from closed to reopened.

Accordingly, the step of outputting comprises outputting the fourth signal to indicate the artery of interest is reopened at that moment.

In an embodiment, w is chosen to be 0.2.

In an embodiment, the cuff pressure is first inflated gradually to occlude the artery of interest, so that the fourth signal indicating the closure of the artery of interest is output, and after the fourth signal indicating the closure of the artery of interest is output, the cuff is further inflated to 20 mmHg-30 mmHg above the inflation SBP and then deflated gradually so that the fourth signal indicating the reopened state of the artery of interest is output.

Furthermore, the first ultrasound signal and the second ultrasound signal are detected synchronously, i.e., operations on the dual ultrasounds should be enabled at the same time, so that the signals detected by using dual ultrasounds are in synchronism with each other. This synchronism remains stable and reliable with respect to patients with arrhythmia or whose heart rate is easily disturbed, since the two blood flows are pulsated from the same source, i.e., the patient's heart.

Other objects and results of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, in which

FIGS. 5*a*-5*c* are detailed flowcharts of the method according to an embodiment of the present invention, wherein FIG. 5*a* is a flowchart for the initialization phase of the method; FIG. 5*b* is a flowchart for determining the moment at which the status of the artery of interest switches from open to closed using cross-covariance based features and FIG. 5*c* is a flowchart for determining the moment at which the status of the artery of interest switches from closed to reopened using cross-covariance based features.

The same reference signs in the figures indicate similar or corresponding features and/or functionalities.

DETAILED DESCRIPTION

The embodiment of the present invention will be described hereinafter in more detail with reference to the drawings.

Figure 1:
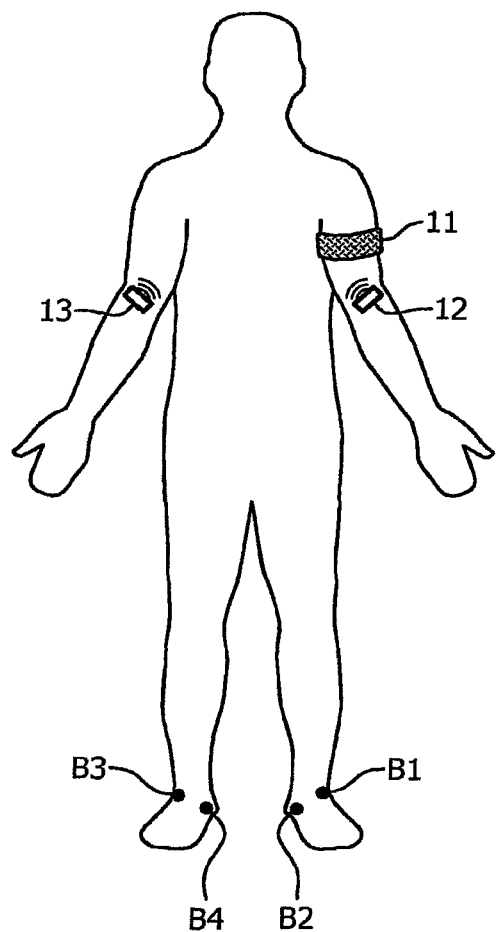
FIG. 1 shows the layout of cuff and dual ultrasound transducers during the ABI measurement.

FIG. 1 presents an example of the layout of the cuff and dual-transducers during ABI measurement.

As can be seen from FIG. 1, the cuff 11 is worn on the left arm to block the brachial artery (the artery of interest). One Doppler ultrasound transducer (the first Doppler ultrasound transducer) 12 is placed on the same arm as the cuff and another Doppler ultrasound transducer (the second Doppler ultrasound transducer) 13 is placed on the reference artery in the other arm without the effect of the cuff. If the two Doppler ultrasound transducers are well positioned, they will sense the blood flow signals of the arteries which are just beneath the transducers.

During the measurement, the signal from the blood flow in the artery of interest detected using the first Doppler transducer 12 will show a sudden change as the artery of interest is occluded by the cuff pressure (inflating SBP) or in an inverse process. The objective of employing another Doppler transducer 13 is to capture the information of the continuous blood flow in the subject's reference artery unobstructed by the cuff pressure throughout the whole measurement.

Regardless of the cuff impact, during the measurement, the two Doppler ultrasound signals detected by using these two transducers should remain highly correlative with one another in spite of the possibility that the sound period, sound power and the device noise vary with respect to time. The subject's stroke output and its period may vary from beat to beat and its impact may be reflected in the signal of the first transducer. The sound source of the two transducers being the same, in the case of successive pulsations coming from the subject's heart, the sound of the second transducer is capable of tracking and following such variance in the signal of the first transducer. Moreover, the distance between the heart and any of the arteries in the same subject is constant, thus ensuring the synchronism of these two sounds.

With the cuff-inflating and deflating operations, the correlation property will drop to a low level when the artery beneath the first transducer is fully occluded and afterwards will rebound to a high level when the artery returns to the open status. Therefore, the moments at which the status of the artery of interest switches from open to closed and from closed to reopened can be determined by means of the angle of the change of the correlation behavior between the dual-transducer signals, and this approach is more stable and more accurate.

Figure 2:
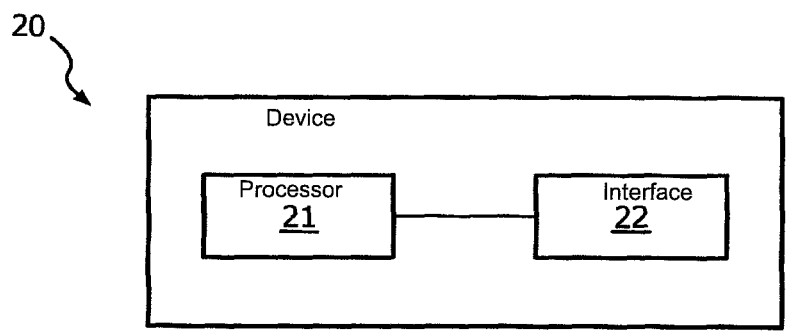
FIG. 2 is a block diagram of the device for determining the open/closed switch moment of an artery of interest under a changing pressure according to an embodiment of the present invention.

FIG. 2 is a block diagram of the device 20 for determining the open/closed switch moment of an artery of interest under a changing pressure according to an embodiment of the present invention.

As can be seen from FIG. 2, the device 20 comprises a processor 21 for deriving a third signal from the first Doppler ultrasound signal and the second Doppler ultrasound signal detected using the two transducers shown in FIG. 1.

The third signal derived by the processor 21 may indicate the degree of synchronism between the first Doppler ultrasound signal and the second Doppler ultrasound signal.

As mentioned above, if the artery of interest is occluded by the cuff pressure in the inflated phase, the first Doppler ultrasound signal detected by using the first Doppler ultrasound transducer should lose synchronism with the second Doppler ultrasound signal detected by using the second Doppler ultrasound transducer; since they are related to the same pulse wave signal of the blood flow of the artery, these two signals should not synchronize with each other if one of the arteries is occluded.

Further, if the artery of interest reopens because the cuff pressure is in the deflated phase, the first Doppler ultrasound signal detected by using the first Doppler ultrasound transducer should recover to synchronize with the second Doppler ultrasound signal detected by using the second Doppler ultrasound transducer, since they are related to the same pulse wave signal of the blood flow of the artery.

As for how to derive the third signal indicating the degree of synchronism between the first Doppler ultrasound signal and the second Doppler ultrasound signal, it will readily occur to those skilled in the art that many signal processing techniques may be used. For example, the cross-covariance property may be used since it is a good indicator of synchronism and it can be directly and easily calculated from the sound domain, thereby enabling it to be achieved in real time. Of course, other parameters or features may be used as long as they indicate the degree of synchronism.

The device 20 further comprises an interface 22 for outputting a fourth signal to indicate that the artery of interest is closed or reopened at the moment when the third signal satisfies a predefined condition.

In an embodiment of the present invention, the third signal is derived from the cross-covariance property between the first Doppler ultrasound signal and the second Doppler ultrasound signal.

In this embodiment, the method of the present invention adopts the cross-covariance property, which is a good indicator of the degree of synchronism. The signal from the first ultrasound transducer correlates well with the signal from the second ultrasound transducer till the measured artery is fully occluded by the cuff pressure. Accordingly, losing the correlation property between two signals and recovering it to a high degree represents the moments at which the status of the artery of interest switches from open to closed and from closed to reopened, respectively, due to the pressure change of the cuff.

Therefore, in accordance with this embodiment, a simple cross-covariance calculation is directly processed on the Doppler audio signal and it can be easily calculated in the sound domain, rather than the frequency domain. The processing time is speeded up so as to meet the real time requirement.

Of course, to determine the degree of synchronism, properties or approaches other than the cross-covariance property may be used to implement the basic idea of the present invention. However, as mentioned above, compared with the cross-covariance property approach, other approaches to determine the degree of synchronism may involve complicated calculations in the frequency domain and may lose some performance as compared to real-time processing.

In a further embodiment of the present invention, the third signal derived from the cross-covariance property between the first ultrasound signal and the second ultrasound signal may comprise at least one of a cross-covariance coefficient of the first and the second ultrasound signals and a lag value of the first and the second ultrasound signals.

In an embodiment, the cuff pressure is first increased gradually to occlude the artery of interest, so that the fourth signal indicating the closure of the artery of interest is output, and after the fourth signal indicating the closure of the artery of interest is output, the cuff is further inflated to 20 mmHg-30 mmHg above the inflation SBP and then deflated gradually, so that the fourth signal indicating the reopened state of the artery of interest is output.

In this embodiment, during the inflation phase, the cuff pressure is increased gradually and the two ultrasound signals are detected by using the two transducers. Either the cross-covariance coefficient of the first and the second ultrasound signals or the lag value of the first and the second ultrasound signals may be derived from these two ultrasound signals, or both may be derived.

After experimental analysis, the inventor finds that if the cross-covariance coefficient is less than 20% of the mean value of the previous values in a certain time window or if abs($L_c$–$L_p$)>w*$L_p$ (wherein $L_c$ is the lag in the current time window, $L_p$ is the mean of lags acquired previously, and w is the adjustable coefficient of the asynchronous tolerance), this may indicate that the two ultrasound signals lose the high correlation property at the moment the status of the artery of interest switches from open to closed.

In an embodiment, w is chosen to be 0.2. Since the asynchronous tolerance relates to the distance between the arteries measured, and the longer the distance between the two arteries, the higher the probability of the risk of blood flow velocity variation, the tolerance is a ratio of the $L_p$ which is proportional to the distance. Normally, w here used is 0.2 to successfully get the differentiator of the state of the artery.

Accordingly, the cuff pressure measured immediately before this determined moment may be determined as the inflation SBP. In other words, the measured inflation SBP reflects the last Doppler sound over the inflation process before the artery is fully occluded.

In this embodiment, after the inflation SBP is determined, the cuff pressure is further increased to 20 mmHg-30 mmHg above the inflation SBP for fully blocking the blood flow to conduct the deflation SBP measurement, as will be readily understood by those skilled in the art.

Subsequently, during the deflation phase, the third signal should be derived from the two ultrasound signals, which third signal comprises both a cross-covariance coefficient of the first and the second ultrasound signals and a lag value of the first and the second ultrasound signals to avoid a false determination.

The inventor has found that if both the cross-covariance coefficient is higher than 20% of the mean value of the previous values and abs(Lc−Lp)<w*Lp, this may indicate that the two ultrasound signals are recovering to again possess a high correlation property at the moment the status of the artery of interest switches from closed to reopened. In this embodiment, w may be chosen to be 0.2 as well.

Accordingly, the cuff pressure measured at that moment may be determined as the deflation SBP.

Furthermore, the first ultrasound signal and the second ultrasound signal are detected synchronously, i.e., operations on the dual ultrasounds should be enabled at the same time so that the signals from dual ultrasounds should be in synchronism with each other. This synchronism remains stable and reliable for patients with arrhythmia or whose heart rate is easily disturbed since the two blood flows are pulsated from the same source, i.e., the patient's heart.

FIG. 3 shows the experimental verification of the present invention on two subjects.

Figure 3A:
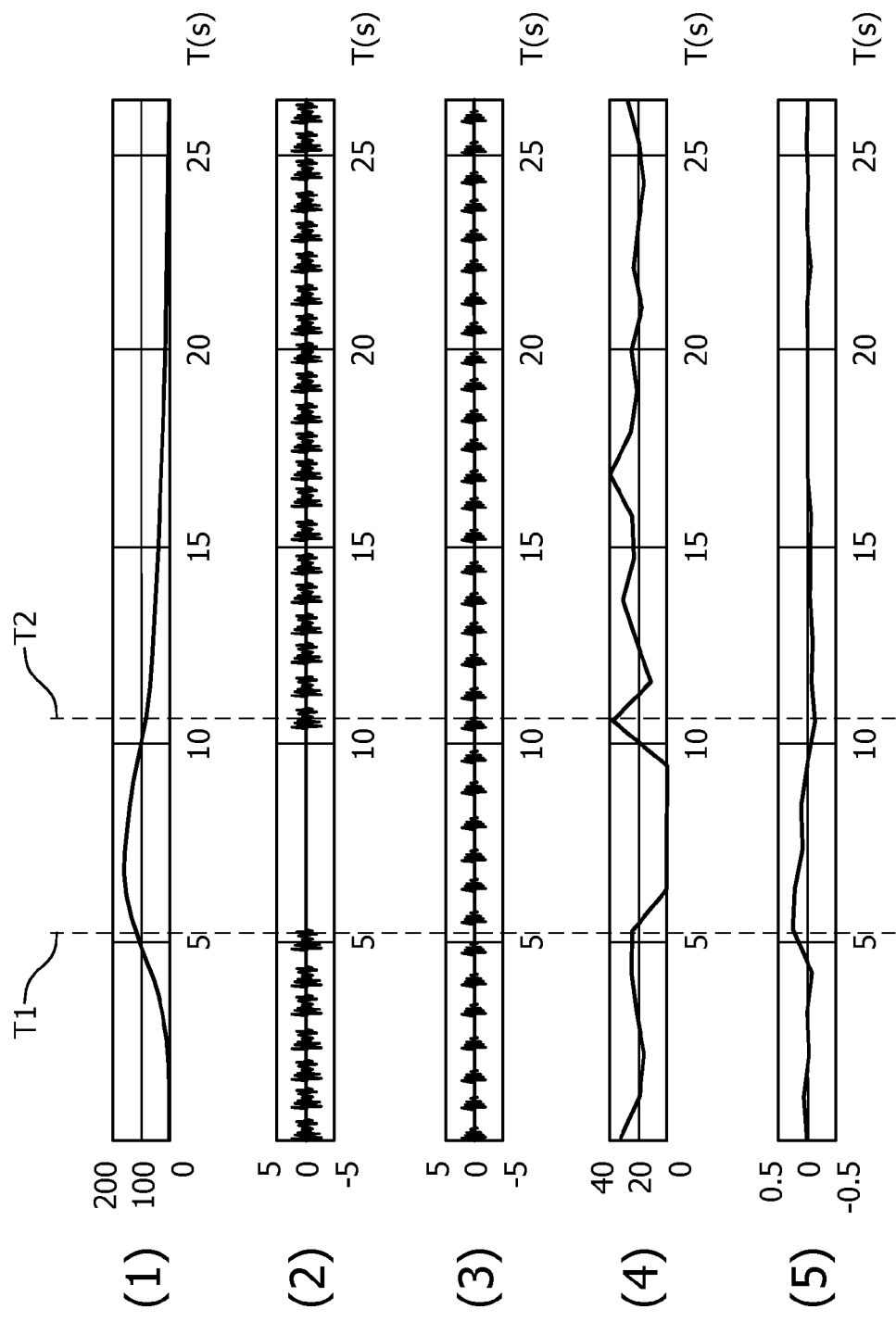
FIGS. 3*a* and 3*b* show the experimental verification of the present invention on two subjects.
Figure 3B:
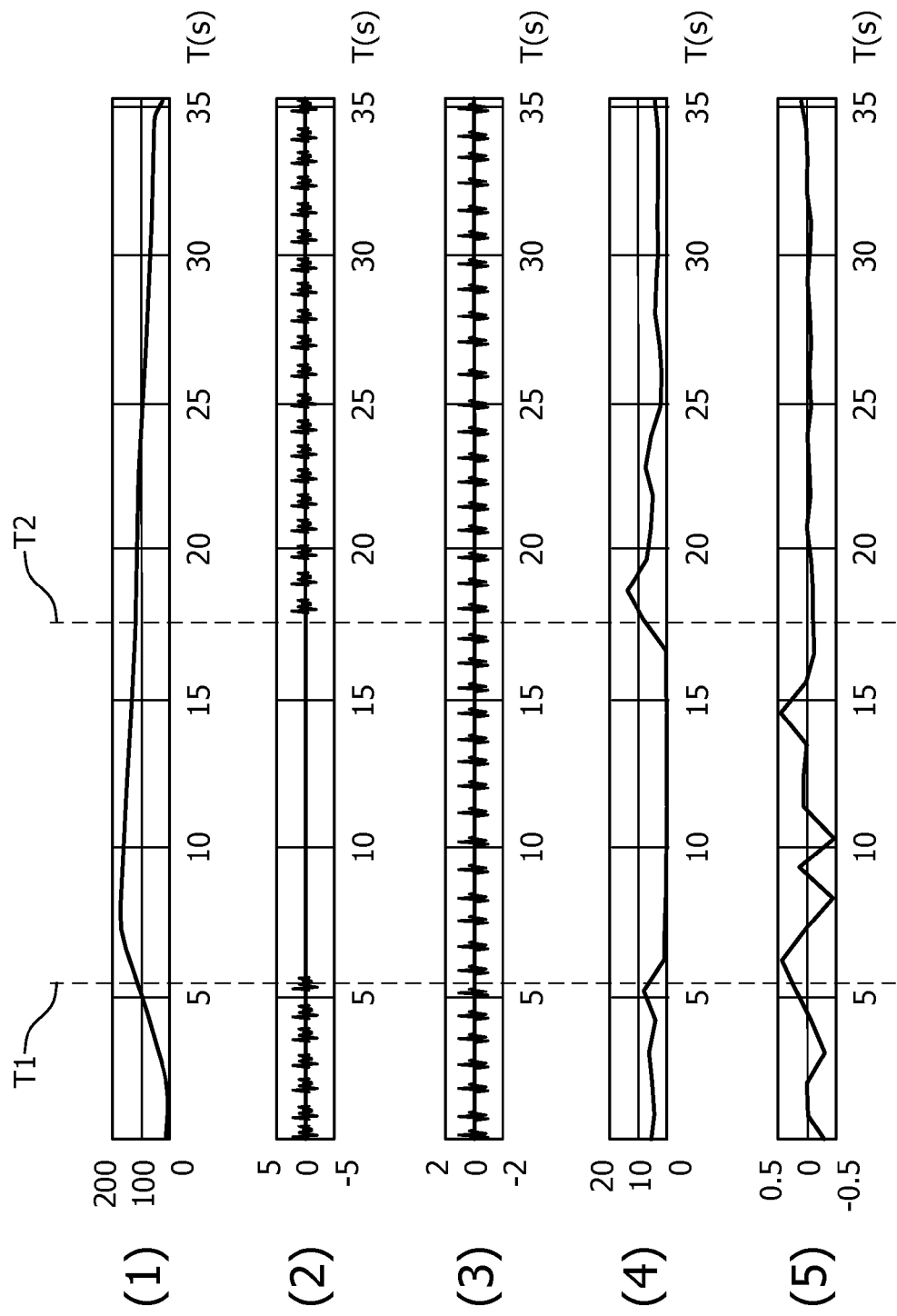

FIGS. 3a and 3b give the result of experimental verification on two subjects, respectively, when the present invention is used for measuring the inflation SBP and the deflation SBP. In these figures, (1) is the cuff pressure signal, (2) and (3) are the audio signals from the two transducers, respectively, (4) and (5) are the time-varying curves of cross-covariance and lags between (2) and (3), respectively. The units of (1)(5) are mmHg, voltage, voltage, null and second.

The closed status period of the artery of interest can be distinctly identified by the section in cross-covariance coefficient curves where the correlation coefficient is lower than the acceptable variance value, which is 20% of the mean value of the previous values in a certain time window adopted in the experiment, or by the section in the lag curve where the lags severely vibrate. According to the start and end time of the sections, the SBP values in inflation and deflation phases can be correspondingly measured from the cuff pressure curve.

The cross-covariance curve in FIG. 3a has an obvious flat section with a low state of the correlation property and its lag curve has an obvious unsteady section with a low state of synchronism. Low correlation or asynchronization with the second transducer's signal indicates the closed status of the artery beneath the first transducer because the artery beneath the second transducer is open from beginning to end.

For example, referring to (4) in FIG. 3a, the moment immediately after T1 represents the moment at which the status of the artery changes from open to closed since the correlation coefficient at that moment is lower than the acceptable variance value, which is 20% of the mean value of the previous values. Furthermore, T2 represents the moment at which the status of the artery changes from closed to reopened since the correlation coefficient rebounds to be higher than 20% of the mean value of the previous values.

Accordingly, in accordance with the standard Doppler ultrasound blood flow measurement, the inflation SBP will be measured at the moment T1, which is the last moment immediately before the determined open-to-closed switch moment, and the deflation SBP will be measured at the moment T2.

This phenomenon is repeatable on the second subject, shown in FIG. 3b, although the power of the sound is smaller and the periodicity of the sound is less regular than that of the first subject. Hence, in spite of the existence of the time-varying periodicity and low signal to noise ratio, either caused by the device or the patient himself, the cross-covariance based feature for deciding the artery status is also stable.

Figure 4:
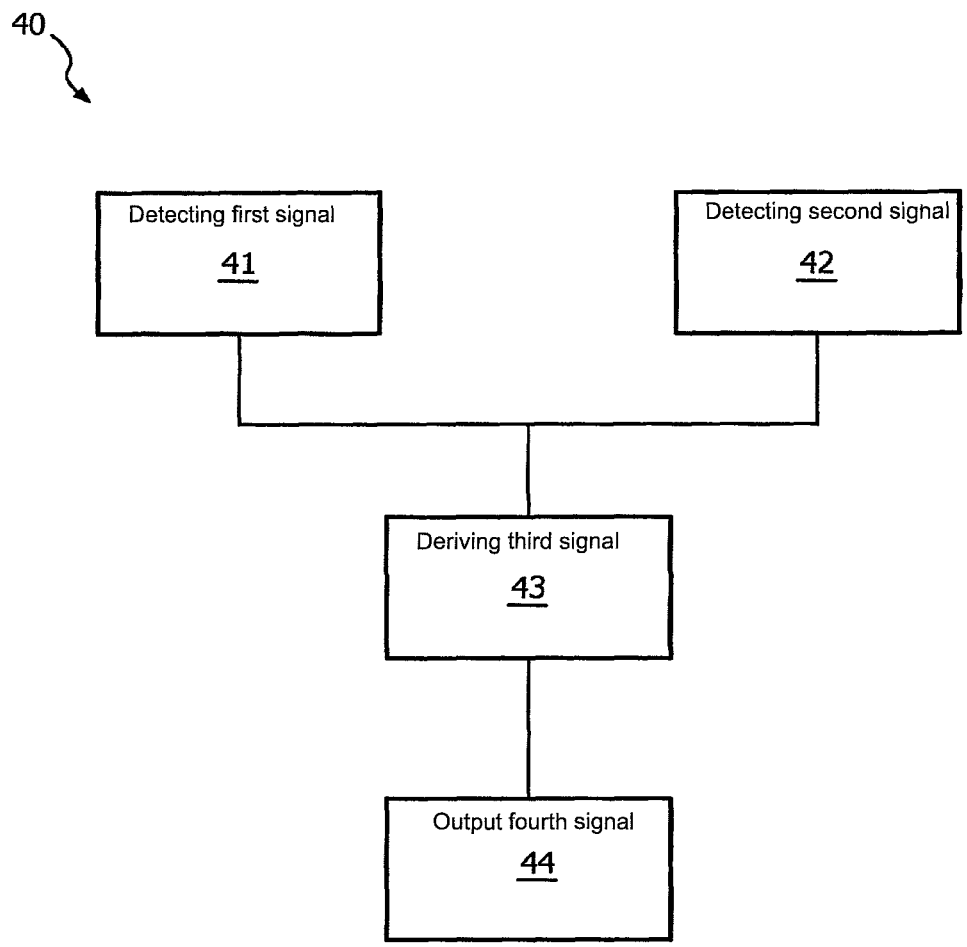
FIG. 4 is a flowchart of the method of determining the open/closed switch moment of an artery of interest under a changing pressure according to an embodiment of the present invention.

FIG. 4 is a flowchart of the method of determining the open/closed switch moment of an artery of interest under a changing pressure according to an embodiment of the present invention.

As shown in FIG. 4, the method 40 according to the present invention comprises a detecting step 41 of detecting a first Doppler ultrasound signal from the blood flow in the artery of interest using a first Doppler ultrasound transducer, which is placed on the artery of interest in one limb wearing a cuff that is capable of being inflated or deflated to provide a changing pressure to the artery of interest.

The method further comprises a detecting step 42 of detecting a second Doppler ultrasound signal from the blood flow in a reference artery using a second Doppler ultrasound transducer. The reference artery may be in any one of the other three limbs.

The method further comprises a deriving step 43 for deriving a third signal from the first Doppler ultrasound signal and the second Doppler ultrasound signal, the third signal indicating the degree of synchronism between the first Doppler ultrasound signal and the second Doppler ultrasound signal. The function of step 43 can be executed by the processor 21 of the device 20 in FIG. 2.

The method further comprises an output step 44 for outputting a fourth signal to indicate that the artery of interest is closed or reopened at the moment when the third signal satisfies a predefined condition. The function of step 44 can be executed by the interface 22 of the device 20 in FIG. 2.

Figure 5A:
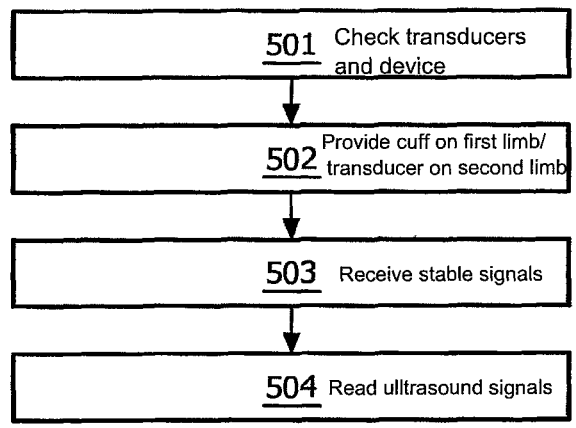
Figure 5B:
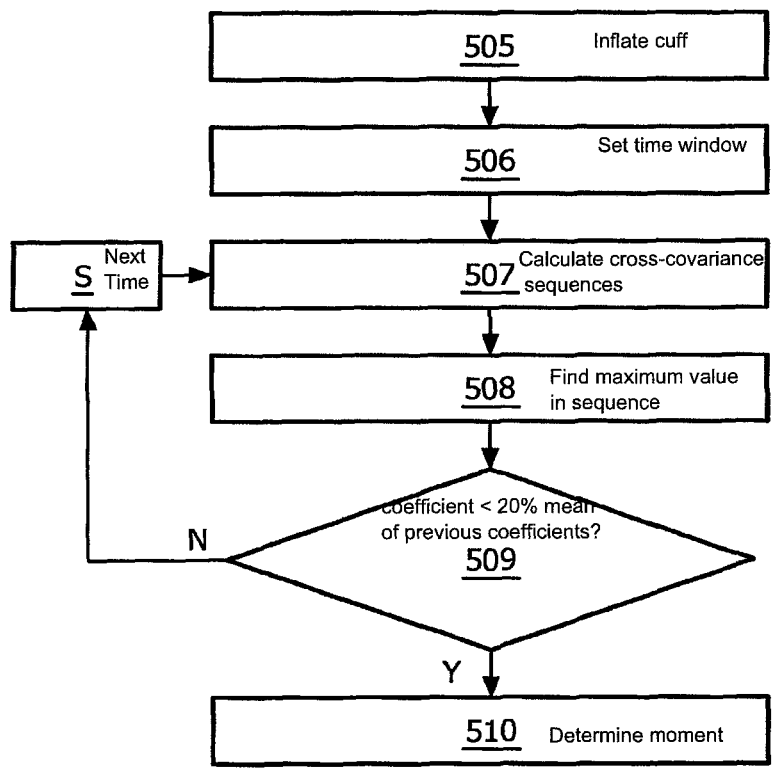
Figure 5C:
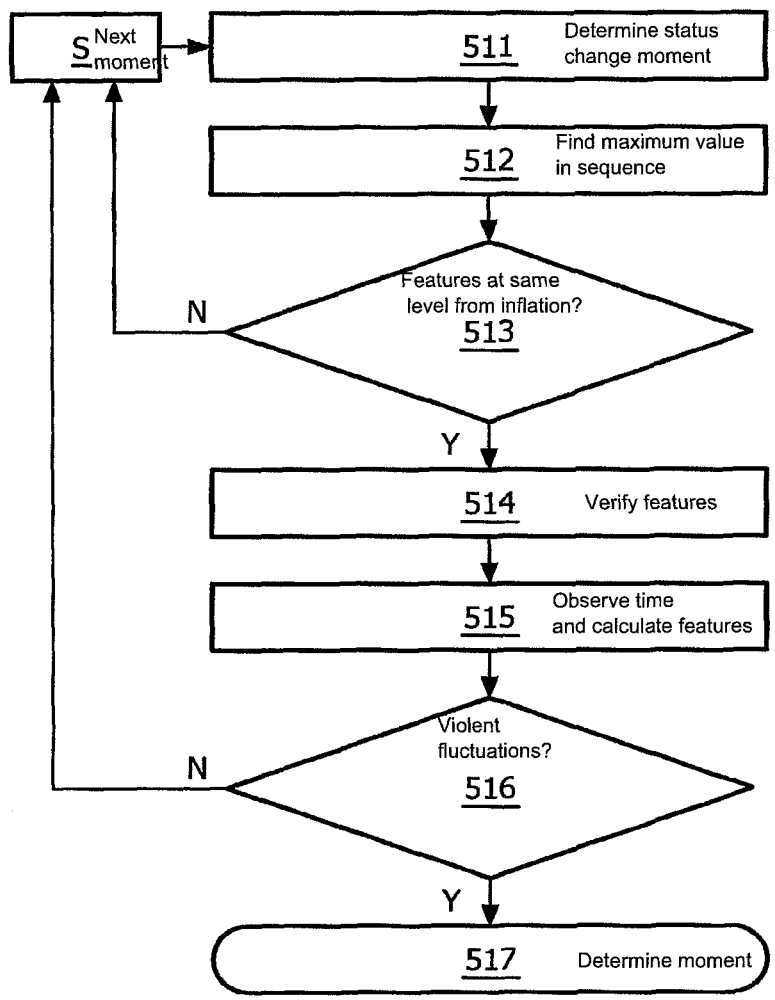

FIG. 5 is a detailed flowchart of the method according to an embodiment of the present invention. The three different phases of initialization, inflation and deflation will be described in detail in conjunction with FIGS. 5a-5c, respectively.

FIG. 5a is a flowchart of the initialization phase of the method. As shown, the initialization phase of this method comprises four steps:

S501: Check whether the dual transducers and the device of the present invention are operating properly and are properly connected together;

S502: Provide the cuff around one limb according to the guideline of ABI measurement, and place one transducer above the artery of interest in this limb and provide another transducer to sense the blood flow in the non-interfered artery (reference artery) in any one of the other three limbs;

S503: Wait several beats until stable Doppler audio signals in rhythm are received, in order to make sure the dual-transducers are well positioned; and S504: Enable two-channel data acquisition at the same time to read simultaneously two Doppler ultrasound signals from the blood flows in the artery of interest and the reference artery, respectively, by using the two transducers.

FIG. 5b is a flowchart for determining the moment at which the status of the artery of interest switches from open to closed using cross-covariance based features. As shown, in this method, the inflation phase to determine the moment at which the status of the artery of interest switches from open to closed comprises the following steps:

S505: Inflate the pressure in the cuff gradually at the proper rate;

S506: Set a sliding time-window with a constant length. The length should be longer than the time of one heart beat to provide at least one pulse in the time-window. Considering the real-time and precision requirement, the length shouldn't be too long either. The number of samples in the time-window, assumed to be N, is determined by the length of the time-window and the data acquisition sampling rate;

S507: After loading N samples in the current time-window in each channel, the cross-covariance sequence of two channel signals in a vector of length 2N−1 is calculated as a function of lag indices;

S508: Find the maximum value in the cross-covariance sequence as the correlation coefficient and the corresponding lag index at the current moment. The current correlation coefficient and lag constitute the current features. The features will be recorded in the memory and will not be forgotten when the current moment is replaced by the next moment due to sliding of the time-window. Accordingly, the features actually are a matrix growing in length over time;

S509: If the current correlation coefficient is less than 20% of the mean of previous coefficients remembered or the lag vibrates towards a big value, the process enters the next step. Meanwhile, the growth of the feature matrix is stopped. Otherwise, slide the window to the next moment (step S in FIG. 5b) and go back to step S507; and S510: Determine the current moment, being the moment at which the status of the artery of interest switches from open to closed.

Furthermore, if the moment at which the status of the artery of interest switches from closed to reopened is also to be determined, the following steps may be performed: Map the moment immediately before the current moment determined above to the cuff pressure, claim the mapped pressure as the inflation SBP, and continue to inflate the pressure to 20 mmHg~30 mmHg above the inflation SBP for fully blocking the blood flow.

FIG. 5c is a flowchart for determining the moment at which the status of the artery of interest switches from closed to reopened using cross-covariance based features. As shown, in this method, the deflation phase to determine the moment at which the status of the artery of interest switches from closed to reopened comprises the following steps:

S511: Since the start moment of deflation is accessible, the time-window fast jumps to the corresponding moment initiating the determining of the moment at which the status of the artery of interest switches from closed to reopened;

S512: Calculate the features in the same way as mentioned in step S508;

S513: If both current features recover to the same level as the feature matrix that has been remembered in the inflation phase, the process enters the next step. Otherwise, slide the window to the next moment (step S in FIG. 5c) and go back to step S512 describing a loop;

S514: Although the current features pass the check of step S513, the following features should still be verified from the viewpoint of stability. Therefore, the current time is only regarded as a suspicious object;

S515: Continue to observe the three successive time-windows or more time and calculate the features item by item;

S516: If none of the features obtained from previous steps shows a violent fluctuation, the process goes to the last step. Otherwise, slide the window over one unit length (step S in FIG. 5c) and return to step S512; and S517: Determine the current moment being the moment at which the status of the artery of interest switches from closed to reopened after passing the cascade checks.

Furthermore, if the method of the present invention for determining the artery status switching moment is utilized to measure blood pressure, the cuff pressure detected at the moment determined as indicated above may be regarded as the deflation SBP. As mentioned above, the SBP thus determined using the present method can be more stable and more reliable regardless of the detailed condition of the subjected users, for the same reason.

It is appreciated that other location options for the second transducer may easily occur to those skilled in the art, enabling the uninterrupted Doppler signals to be easily acquired on the skin surface as the reference sound, such as the positions B1~B4 in FIG. 1.

B1 and B3 are dorsalis pedis arteries (DPA) on the bilateralis of the lower limbs. B2 and B4 are posterior tibial arteries (PTA) on the bilateralis of the lower limbs. It is well known that all six arteries at the positions of the two transducers 12, 13 and B1~B4 shown in FIG. 1 should be measured by conducting an ABI measurement, so that the automatic ABI measurement needs six Doppler transducers to sense the blood flows through these arteries. In this invention, although dual transducers are necessary for single limb SBP measurement, the additional cost can be avoided by using six transducers alternatively. For example, if the operator tries to measure the SBP value of either PTA or DPA on the lower left limb, the reference sound can be collected from any one of the transducers at 12, 13, B3 and B4 in FIG. 1. The rule can be abstracted as follows: if the cuff is placed on one limb, the reference sound comes from any transducer on the other three limbs.

Furthermore, as is easily understood by those skilled in the art, the above described method and device for determining the open/closed switch moment of an artery of interest under a changing pressure can be used in a system which comprises the device 20 according to the present invention and two Doppler ultrasound transducers 12 and 13, the first Doppler ultrasound transducer 12 being placed on the artery of interest in one limb which is provided with a cuff and the second Doppler ultrasound transducer 13 being placed on a reference artery in any one of the other three limbs, without the effect of the cuff.

Furthermore, as mentioned above, the method of the present invention may be utilized in SBP measurement but is not limited thereto. Since the status switch moment of the artery is very important in the blood flow measurement, it may be used for some other purposes as well.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A method of determining a moment at which a status of an artery of interest under a changing pressure switches from open to closed and from closed to reopened, the method comprising:

detecting a first Doppler ultrasound signal from the blood flow in the artery of interest using a first Doppler ultrasound transducer, which is adapted to be placed on skin overlying an artery of interest in a first limb which is wearing a cuff that is capable of being inflated or deflated to provide the changing pressure to the artery of interest;

detecting a second Doppler ultrasound signal from the blood flow in a reference artery using a second Doppler ultrasound transducer, the second Doppler ultrasound transducer being adapted to be placed on skin overlying a reference artery in a second limb that is different from the first limb;

deriving a third signal from a cross-covariance property between the first Doppler ultrasound signal and the second Doppler ultrasound signal, the third signal indicating a degree of synchronism between the first Doppler ultrasound signal and the second Doppler ultrasound signal; and outputting a fourth signal to indicate whether the artery of interest is closed or open based on whether the third signal satisfies a predefined condition.

2. The method of claim 1, wherein
the third signal comprises at least one of a cross-covariance coefficient of the first and the second Doppler ultrasound signals and a lag value of the first and the second Doppler ultrasound signals.

3. The method of claim 2, wherein
the third signal satisfies the predefined condition if the cross-covariance coefficient is less than 20% of a mean value of the previous values or abs(Lc−Lp)>w*Lp, wherein Lc is the lag value of the first and second Doppler ultrasound signals in a current time window, Lp is a mean value of lag values acquired in previous time windows, and w is an adjustable coefficient of the asynchronous tolerance, and the outputting comprises outputting the fourth signal to indicate the artery of interest is closed when the third signal satisfies the predefined condition if the cross-covariance coefficient is less than 20% of a mean value of the previous values or abs(Lc−Lp)>w*Lp.

4. The method of claim 3, wherein w is 0.2.

5. The method of claim 1, wherein
the third signal comprises a cross-covariance coefficient of the first and the second Doppler ultrasound signals and a lag value of the first and the second Doppler ultrasound signals, and the third signal satisfies the predefined condition if both the cross-covariance coefficient is higher than 20% of the mean value of the previous values and abs(Lc−Lp)<w*Lp, wherein Lc is the lag value of the first and second Doppler ultrasound signals in a current time window, Lp is the mean value of the lag values acquired in previous time, and w is an adjustable coefficient of the asynchronous tolerance, and the outputting comprises outputting the fourth signal to indicate the artery of interest is open when the third signal satisfies the predefined condition if both the cross-covariance coefficient is higher than 20% of the mean value of the previous values and abs(Lc−Lp)<w*Lp.

6. The method of claim 1, further including:
increasing the cuff pressure to occlude the artery of interest, so that the fourth signal indicating the closure of the artery of interest is output, and after the fourth signal indicating the closure of the artery of interest is output, further inflating the cuff to 20 mmHg-30 mmHg above an inflating systolic blood pressure and then deflating the cuff gradually, so that the fourth signal indicating the open state of the artery of interest is output.

7. The method of claim 1, wherein
the first Doppler ultrasound signal and the second Doppler ultrasound signal are detected synchronously.

8. A device for determining a moment at which a status of an artery of interest under a changing pressure switches from open to closed and from closed to reopened, the device comprising:
a first Doppler ultrasound transducer adapted to detect a first Doppler ultrasound signal from the blood flow in the artery of interest, the first Doppler ultrasound transducer being adapted to be placed on skin overlying an artery of interest in a first limb wearing a cuff that is capable of being inflated or deflated to provide the changing pressure to the artery of interest;

a second Doppler ultrasound transducer adapted to detect a second Doppler ultrasound signal from the blood flow in a reference artery, the second Doppler ultrasound transducer being adapted to be placed on skin overlying a reference artery in a second limb that is different from the first limb;

one or more processors adapted to:
derive a third signal from the first Doppler ultrasound signal and the second Doppler ultrasound signal, the third signal indicating the degree of synchronism between the first Doppler ultrasound signal and the second Doppler ultrasound signal; and output a fourth signal to indicate the artery of interest is closed or open when the third signal satisfies a predefined condition.

9. The device of claim 8, wherein the one or more processors is adapted to derive
the third signal from a cross-covariance property between the first Doppler ultrasound signal and the second Doppler ultrasound signal.

10. The device of claim 9, wherein the one or more processors is configured to output the fourth signal in response to:
the third signal comprising a cross-covariance coefficient of the first and the second Doppler ultrasound signals and a lag value of the first and the second Doppler ultrasound signals, and the third signal satisfying the predefined condition if both the cross-covariance coefficient is higher than 20% of the mean value of the previous values and abs(Lc−Lp)<w*Lp, wherein Lc is the lag value of the first and second Doppler ultrasound signals in a current time window, Lp is the mean value of lag values acquired in previous time, and w is an adjustable coefficient of the asynchronous tolerance.

11. The device of claim 8, wherein the one or more processors is configured to derive the third signal by:
deriving at least one of a cross-covariance coefficient of the first and the second Doppler ultrasound signals and a lag value of the first and the second Doppler ultrasound signals.

12. The device of claim 11, wherein the one or more processors is configured to output the fourth signal in response to:
the third signal satisfying the predefined condition of the cross-covariance coefficient is less than 20% of a mean value of the previous values or abs(Lc−Lp)>w*Lp, wherein Lc is the lag value of the first and second Doppler ultrasound signals in a current time window, Lp is the mean value of the lag values acquired in previous time, and w is an adjustable coefficient of the asynchronous tolerance.

13. A device for determining a moment at which a status of an artery of interest under a changing pressure switches from open to closed and from closed to reopened, the device comprising:
- a first Doppler ultrasound transducer adapted to detect a first Doppler ultrasound signal from the blood flow in the artery of interest, the first Doppler ultrasound transducer being adapted to be placed on skin overlying an artery of interest in a first limb;
- a second Doppler ultrasound transducer adapted to detect a second Doppler ultrasound signal from the blood flow in a reference artery, the second Doppler ultrasound transducer being adapted to be placed on skin overlying a reference artery in a second limb that is different from the first limb;
- at least one processor programmed to:
  - receive the first and second Doppler ultrasound signals from the corresponding first and second Doppler ultrasound transducers; and
  - derive a synchrony signal from the received first and second Doppler ultrasound signals, the derived signal indicating a comparison of synchrony between the first and second Doppler ultrasound signals; and
- a display configured to display an indication that comparison of synchrony between the first and second Doppler ultrasound signals is below a predefined threshold to indicate the artery of interest is closed or open.

14. The device of claim 13, wherein the at least one processor is programmed to derive the synchrony signal from a cross-covariance property between the first Doppler ultrasound signal and the second Doppler ultrasound signal.

15. The device of claim 14, wherein the at least one processor is programmed to derive the synchrony signal including at least one of a cross-covariance coefficient of the first and the second Doppler ultrasound signals and a lag value of the first and the second Doppler ultrasound signals.

16. The device of claim 15, wherein the at least one processor is programmed to control the display to display the indication that the artery of interest is closed in response to the synchrony signal satisfying a predefined condition of the cross-covariance coefficient being less than 20% of a mean value of the previous values or $abs(Lc-Lp)>w*Lp$, wherein $Lc$ is the lag value of the first and second Doppler ultrasound signals in a current time window, $Lp$ is the mean value of the lag values acquired in previous time, and $w$ is an adjustable coefficient of the asynchronous tolerance.

17. The device of claim 14, wherein the at least one processor is programmed to:
- determine a cross-covariance coefficient of the first and the second Doppler ultrasound signals and a lag value of the first and the second Doppler ultrasound signals, when the synchrony signal satisfies a predefined condition of both the cross-covariance coefficient being higher than 20% of the mean value of the previous values and $abs(Lc-Lp)<w*Lp$, wherein $Lc$ is the lag value of the first and second Doppler ultrasound signals in a current time window, $Lp$ is the mean value of lag values acquired in previous time, and $w$ is an adjustable coefficient of the asynchronous tolerance; and
- control the display to display the indication that the artery of interest is open when the third signal satisfies the predefined condition.

18. The device of claim 13, further including:
- a cuff configured for attachment to the first limb, the cuff being configured to be inflated or deflated to provide the changing pressure to the artery of interest;
- wherein the cuff pressure is first gradually increased to occlude the artery of interest, so that the indication of the closure of the artery of interest is displayed on the display, and
- after the indication of the closure of the artery of interest is displayed, the cuff is further inflated to 20 mmHg-30 mmHg above an inflating systolic blood pressure and then deflated gradually, so that the fourth signal indicating the open state of the artery of interest is output.

* * * * *